United States Patent [19]

Shaya et al.

[11] Patent Number: 5,447,164
[45] Date of Patent: Sep. 5, 1995

[54] INTERACTIVE MEDICAL INFORMATION DISPLAY SYSTEM AND METHOD FOR DISPLAYING USER-DEFINABLE PATIENT EVENTS

[75] Inventors: Mousa N. Shaya, Acton, Mass.; Michael C. Higgins, Palo Alto, Calif.; Wai-Ling Hew, Nashua, N.H.

[73] Assignee: Hewlett-Packard Company, Palo Alto, Calif.

[21] Appl. No.: 148,709

[22] Filed: Nov. 8, 1993

[51] Int. Cl.⁶ ............................................... A61B 5/0402
[52] U.S. Cl. ..................................... 128/710; 128/700
[58] Field of Search ............... 182/696, 700, 705, 706, 182/709, 710, 712

[56] References Cited

U.S. PATENT DOCUMENTS

| | | | |
|---|---|---|---|
| 3,779,237 | 12/1973 | Goeltz et al. | |
| 4,340,065 | 7/1982 | Gessman | 128/712 |
| 4,414,981 | 11/1983 | Wong et al. | 128/712 |
| 4,625,278 | 11/1986 | Wong | 364/417 |
| 4,776,345 | 10/1988 | Cohen et al. | 128/731 |
| 4,779,199 | 10/1988 | Yoneda et al. | 364/413.03 |
| 4,914,568 | 4/1990 | Kodosky et al. | 364/200 |
| 5,020,011 | 5/1991 | Stark et al. | 364/580 |
| 5,047,930 | 9/1991 | Martens et al. | 364/413.04 |
| 5,086,778 | 2/1992 | Mueller et al. | 128/696 |
| 5,090,418 | 2/1992 | Squires et al. | 128/702 |
| 5,139,027 | 8/1992 | Lindecrantz | 128/696 |

*Primary Examiner*—William E. Kamm
*Assistant Examiner*—Scott M. Getzow

[57] ABSTRACT

An interactive medical information display system and method for displaying user-definable patient events is provided. The system includes a mechanism for acquiring physiological parameters from a patient and a mechanism for storing the parameters in a real-time database. In addition, the system includes a mechanism for users to define event types in an event defintion language and a mechanism for users to modify existing event types. Users then select a set of event types for display, and an event generator accesses the database to monitor the physiological parameters in order to detect event occurrences as defined by the event types. A display mechanism displays the event occurrences and provides users with the ability to select event occurrences randomly or sequentially. Upon selection, other information is displayed.

17 Claims, 11 Drawing Sheets

INTERACTIVE MEDICAL INFORMATION DISPLAY SYSTEM AND METHOD FOR DISPLAYING USER-DEFINABLE PATIENT EVENTS

FIELD OF THE INVENTION

This invention relates to medical information display systems that access patient information in a computerized database. More particularly, this invention relates to real-time, interactive medical information systems that store patient information and display that information as user-definable events.

BACKGROUND OF THE INVENTION

In the past, paper-based flow sheets, located at a patient's bedside, were typically used in hospitals to store medical data concerning that patient. This method was time-consuming and costly.

More recently, hospitals have turned to computer technology to store and view patient information at the patient's bedside. An example of such a system is the Carevue 900 system, manufactured and sold by Hewlett-Packard Company, Clinical Information Systems. These systems chronologically display on a computer screen a predetermined set of trend data that are derived from data that are sensed by transducers attached to the patient. A typical display is shown in FIG. 1.

In these systems, the clinician is forced to scan the information in a basically sequential fashion. Moreover, the displayed information is typically limited to directly measurable physical quantities or trend data derived therefrom. Sequential scanning is time consuming, and the displayed information can be over- or under-informative from the perspective of the clinician.

Clinicians, when analyzing a patient, are generally interested in "events." Events are constructs involving relationships among different measurements. For example, an event can be a particular measurement occurring at a particular rate, or attaining a particular threshold. In addition, an event can be the concurrence of several measurements attaining particular thresholds or occurring at particular rates.

For example, hypothermia is a condition of abnormally low body temperature. This condition can be serious if it lasts for an extended period. Thus, a clinician may wish to detect if the patient's body temperature was below 92° F. for a duration greater than one hour. In addition, symptomatic tachychardia is a condition in which the heart rate is very fast and the resulting blood pressure drops below a certain level. Thus, a clinician may wish to detect when the patient's heart rate was greater than 180 beats per minute for a duration greater than 30 seconds and detect whether the patient's systolic arterial blood pressure was less than 80 mmHg for a duration greater than 30 seconds.

If they had their choice, clinicians would prefer to directly view event occurrences on the computer screen. Moreover, they would prefer to tailor event definitions on a per-patient basis, and they would prefer the ability to scan through events and data related to those events in a random as well as a sequential manner. Clinicians also prefer the ability to tailor the list of displayed events.

SUMMARY OF THE INVENTION

The present invention provides methods and apparatus for identifying and displaying events in a medical information system. The medical information system comprises a patient monitoring device for acquiring physiological parameters from a patient, a computer system for processing the physiological parameters acquired from the patient to provide medical information and a display unit for displaying the medical information to a user. In accordance with the method, the medical information system establishes an event associated with the patient. The event is defined by a user in an event definition language and includes an event definition which defines the event as having an occurrence when one or more of the physiological parameters meets a prescribed condition. The physiological parameters are acquired in real time and are monitored for occurrences of the event. The user is informed of occurrences of the event.

Typically, the occurrences of the event are displayed as a function of time on the display unit. Preferably, the occurrences of the event are displayed on a time line. Preferably, a count of the occurrences of the event is displayed on the display unit. As a further feature, detailed information regarding an occurrence of the event selected by the user can be displayed on the display unit. The detailed information can include a waveform of one of the physiological parameters in a time interval corresponding to the occurrence of the event selected by the user.

The acquired phsyiological parameters can be monitored for occurrences of the event as they are acquired from the patient. The physiological parameters acquired over a prescribed time period are stored. In an alternative monitoring mode, the stored physiological parameters are searched for occurrences of the event. A new event can be established during or after acquisition and storage of the physiological parameters. In this case, the stored physiological parameters are searched for occurrences of the new event.

The events can be defined in the event definition language by a wide variety of relationships. A first event type can be defined by a relationship between one of the physiological parameters and a numerical value. A second event type can be defined by a relationship involving a logical combination of two or more conditions met by the physiological parameters. A third event type can be defined by a relationship involving an arithmetic operation upon one or more of the physiological parameters. A fourth event type can be defined by a relationship involving a timing operation with respect to one or more of the physiological parameters. A fifth event type can be defined by a relationship involving a minimum or maximum value of one of the physiological parameters. A sixth event time can be defined by a relationship involving one or more previously defined events.

DETAILED DESCRIPTION

To improve the informational content of patient information display systems and to improve functional access to that information, the present invention comprises a medical information display system and method, wherein the display system has a mechanism for receiving and storing patient measurements in a database in real-time, and wherein the computer display system has a mechanism for accessing that stored digital data and processing that data according to event type definitions that are stored in the database and that can be interactively created and modified by the user. The display system has a mechanism for storing in the database the processed events so that they can be retrieved by a mechanism for displaying the stored events on a computer screen.

In the invention, a subset of the stored event types are displayed on a computer screen. For each displayed event type, there is a corresponding event time line with tick marks indicating the instances when that event occurred. The duration of the time lines is displayed and is user-modifiable.

Particular occurrences of an event can be selected, either sequentially or randomly. Upon such selection, several other features of the event or the occurrence are displayed, such as waveforms, text, images, and user performed measurements. The duration of the waveform is also user-modifiable.

Ancillary menus, or dialog boxes, can be activated from the main screen or from other ancillary menus. The ancillary menus provide further mechanisms for the user to tailor the output of the main screen or to tailor the definition of the stored event types.

The event type definitions can be created and tailored to a particular patient. This tailoring and creation can be performed interactively.

Figure 1:
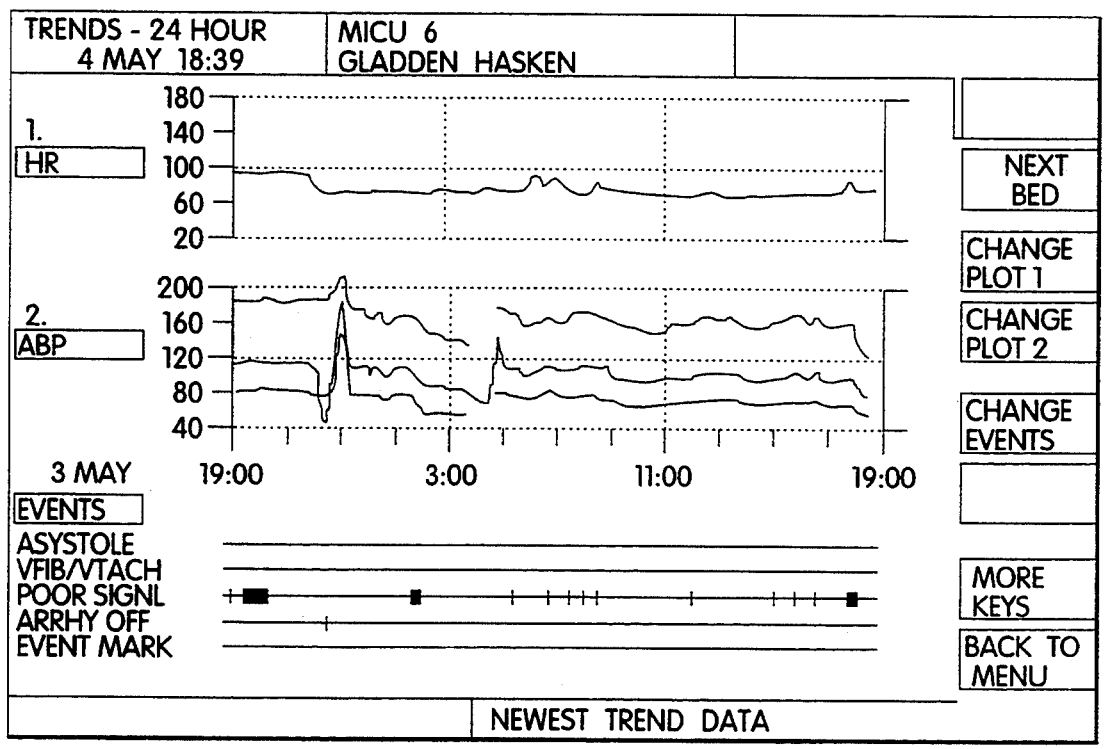
FIG. 1 is a screen display of a prior art medical information display system
Figure 2:
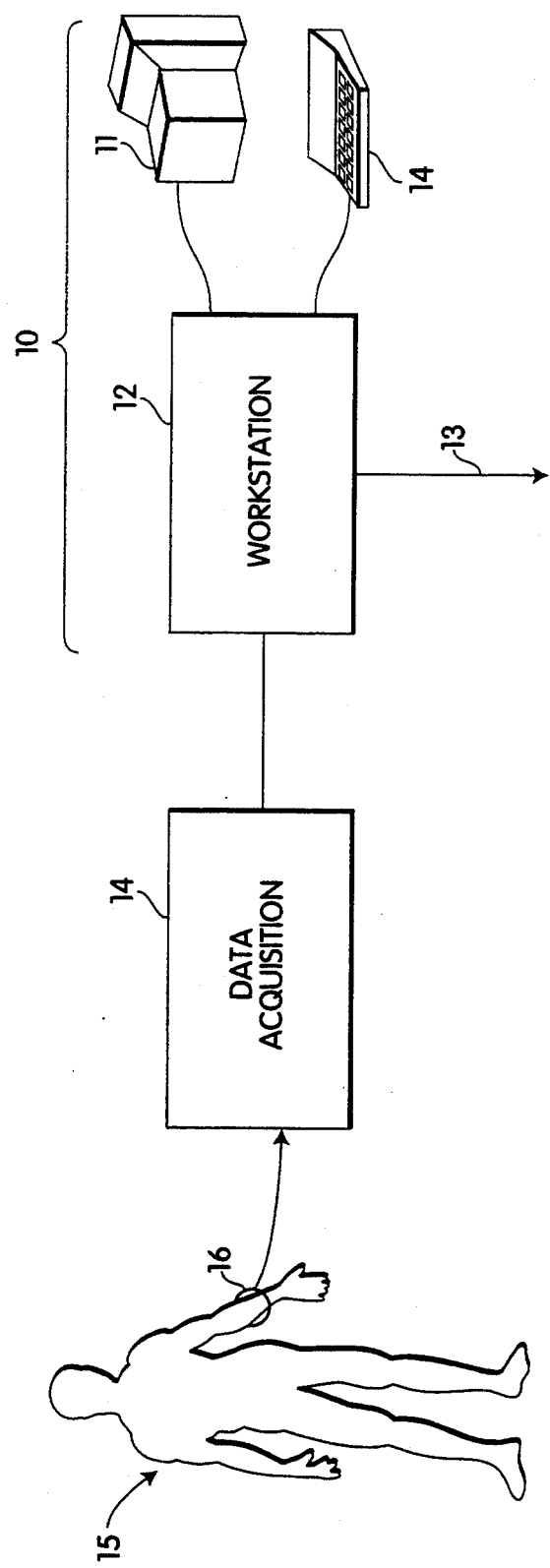
FIG. 2 is a block diagram of the medical information display system hardware.

FIG. 2 illustrates an example of a medical information display system 10 that may be used to display patient information on a display screen of a monitor 11. A patient 15 is connected to one or more sensors 16 for measuring patient data. This information is received by a bedside data acquisition system 14, which converts the received data into a digital format and transfers that information to a workstation 12 of display system 10. Optionally, workstation 12 can be connected to a local area network ("LAN") 13. A clinician can enter data and commands into display system 10 via an input device 14.

Figure 3:
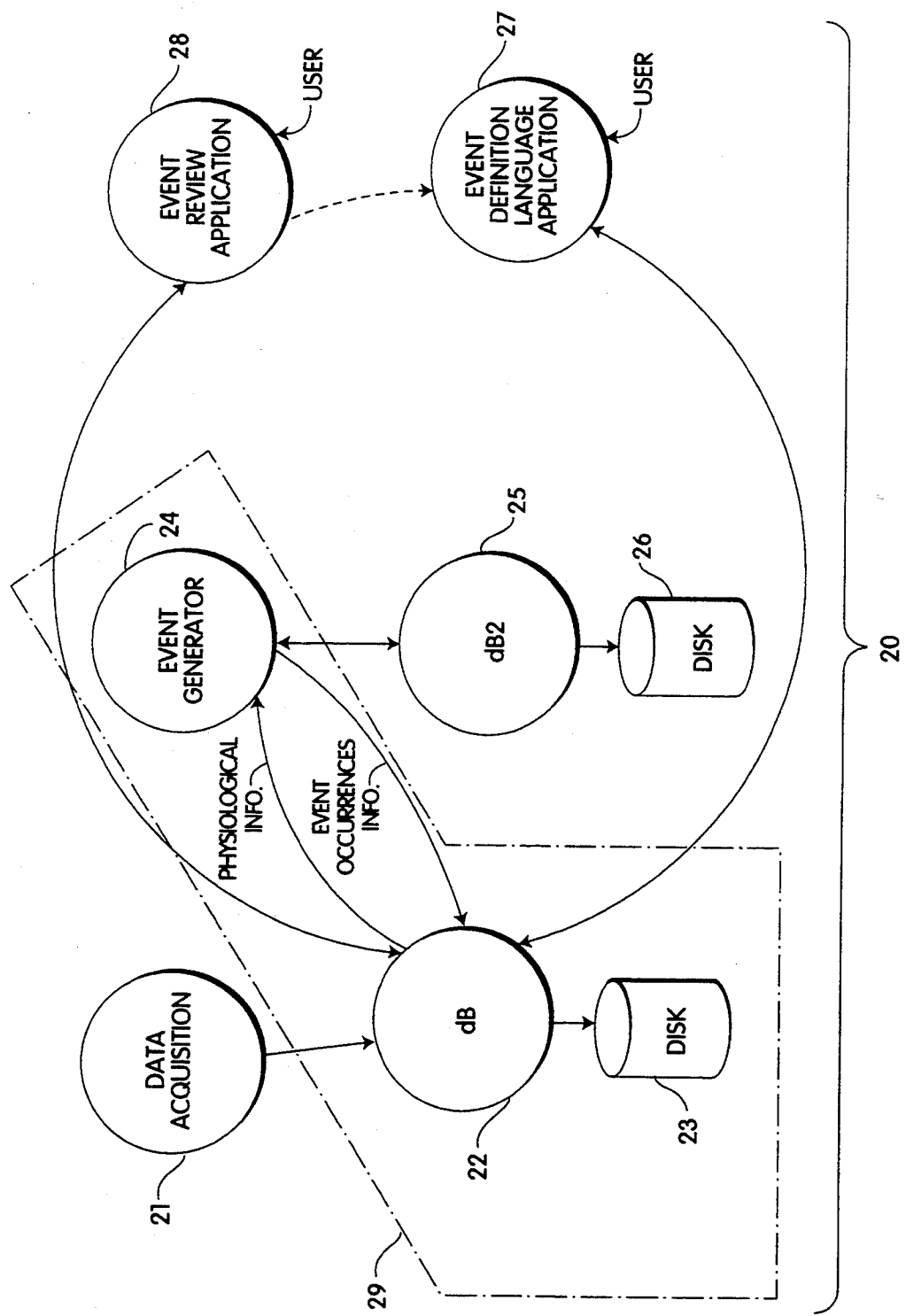
FIG. 3 is a block diagram of the present invention.

FIG. 3 illustrates the software architecture 20 of display system 10, schematically interacting with hardware disks 23, 26. It will be appreciated by those skilled in the art that the invention described herein may be implemented on various platforms. In a preferred embodiment, however, the invention utilizes a HP Appolo Series 700 Model 715/50, with 256 MB of main memory and 2/68.6 GB of disk storage. Further, a preferred embodiment utilizes the C and the C++ computer languages for the various software modules, and the UNIX operating system to control workstation 12 including the various software modules. Furthermore, software relating to the user interface is implemented using the Motif graphics package, a graphics package known in the art. It will be appreciated by those skilled in the art that alternative languages, operating systems, and graphics packages may be employed.

To briefly outline the interaction of the various software elements of FIG. 3, the data acquisition system 21 receives patient information and writes it to a disk 23 via a database application 22 ("database"). An Event Definition Language Application ("EDL") 27 provides the user with the ability to define events as a combination of relations and conditions of stored patient information. For example, as stated above, the event "hypothermia" may be defined as a patient's body temperature being below a certain level for a certain duration. The event definitions are stored in database 22 as a dictionary, where they are accessible by an Event Review Application ("ERA") 28 and an Event Generator 24. The user selects a set of events for display via ERA 28. This selection is eventually communicated to the Event Generator 24. When triggered, the Event Generator 24 monitors all or a portion of the stored patient information in accordance with the selected event definitions. The Event Generator 24 detects any event occurrences and communicates such information to the database 22. Upon such communication, the database 22 informs the ERA 28, which will then retrieve the occurrence information so that it may be displayed.

Figure 10:
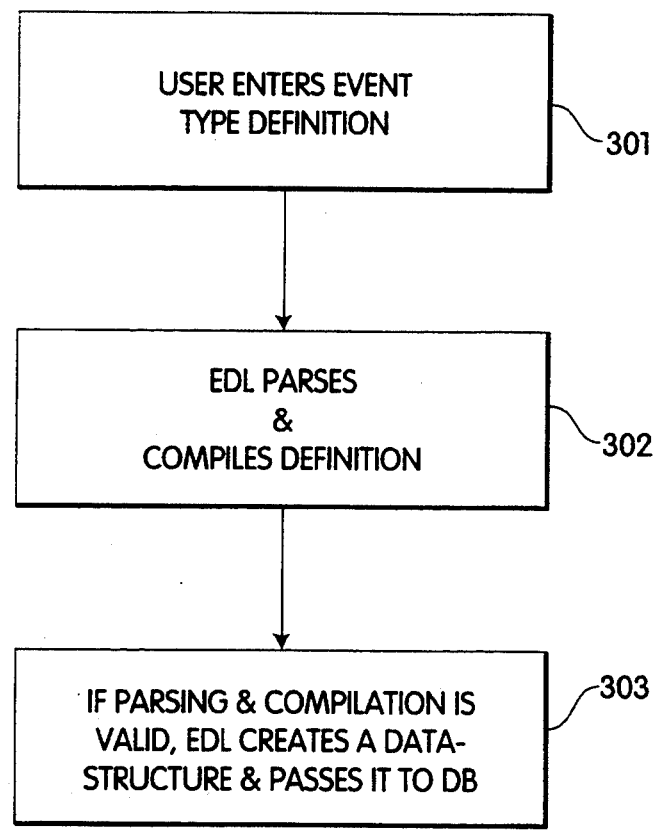
FIG. 10 illustrates the steps of creating and entering event type definitions in a preferred embodiment of the invention.

In order to gain a fuller appreciation of the invention, refer to FIG. 3. and FIG. 10, which illustrates the several steps leading to the storing of an event type definition into the database. The user enters an event type definition (step 301) FIG. via EDL 27. Then, EDL 27 parses the definition for correct syntax and compiles the definition into a definition data structure (step 302). This definition data structure is then passed (step 303) to the database 22 to be stored in the definition dictionary, where it is available for the user to select via the ERA 28.

Figure 11:
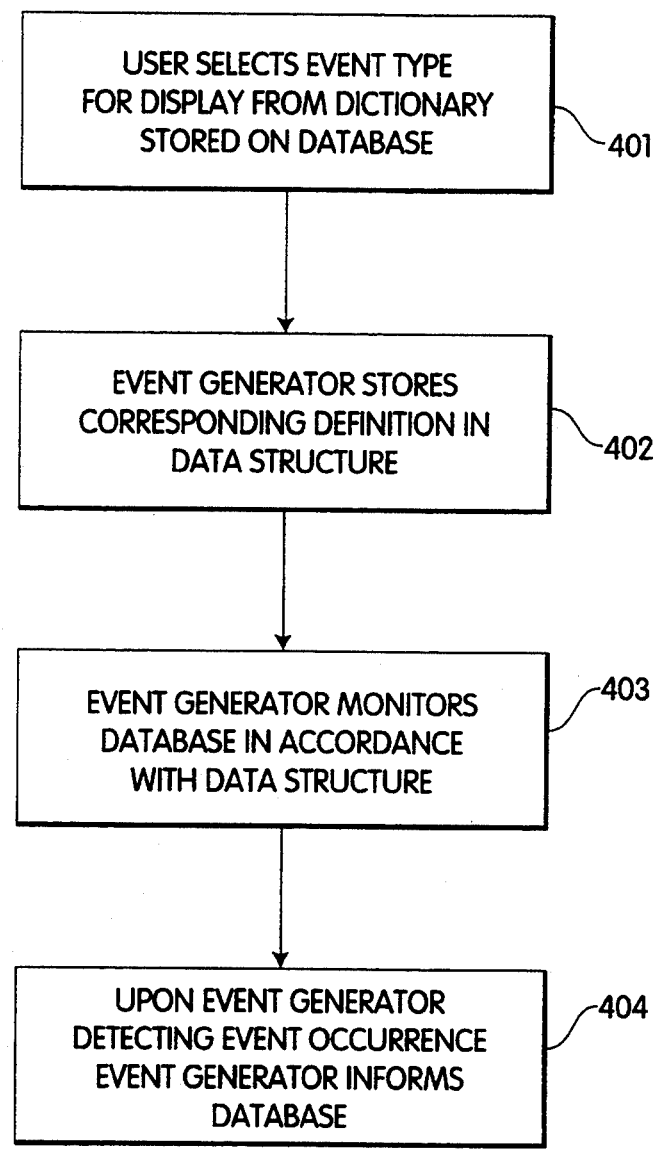
FIG. 11 illustrates the steps of selection and detection of event types in a preferred embodiment of the invention.

Now, refer to FIG. 3. and FIG. 11, which illustrates the steps leading to the displaying of any event occurrences for a newly selected event type. The user selects the desired event type from the dictionary (step 401) via ERA 28. The event generator 24 communicates with the database 22 to determine which event type definition has been selected, so that the event generator 24 can update an internal data structure accordingly step 402. The event generator 24 monitors the database for a time period selected by the user. As such, it monitors all the patient information that is implicated by the set of event type definitions stored in the event generator's data structure step 403. The event generator 24 informs database 22, via a message, upon detecting event occurrences step 404.

The event generator 24, the database 22, and the disk system 23 comprise a server 29. The ERA 28 and the EDL 27 are each clients. The terms "client" and "server" are known in the art.

The data acquisition module 21 receives the digital patient data and transfers that data to database 22. Data acquisition system 21 is comprised of drivers and other software modules known in the art, which are not further described in this application for the sake of clarity.

Database 22 writes the data received from data acquisition system 21 to disk system 23. In a preferred embodiment, database 22 is a temporal database. A temporal database is one in which the disks are organized such that the location of the data implicitly contains information concerning when the data was written to the disk. In this fashion, a separate data, one explicitly stating the time of the data entry, need not be included. The temporal database contains data representing a moving window of time. The database does not preclude the use of explicit time stamps for data, and in some instances, it may be best to use an explicit time stamp, for example, in the case of manually measured blood pressure. However, certain data, such as ECG waveforms, are best suited for implicit time stamping because they occur at fixed intervals in time and are continuous.

In addition, this database is a "real-time" database, as the term is commonly understood in the art. In particular, the interrupt response time of the event generator is of the order of one minute.

The event generator 24, when triggered into action, monitors the patient information stored in disk system 23 in order to detect event occurrences. It monitors the patient information in accordance with a time period selected by the user and in accordance with the set of event type definitions that are selected by a user for display. If the event generator 24 detects that the conditions and relations that constitute an event definition have been met, i.e., if the event generator detects an event occurrence, it informs database 22 accordingly.

The event generator 24 includes an internal data structure for storing the set of event type definitions needed for display. The data structure need only include those definitions that are directly, or indirectly, necessary for the events that are selected for display. Events are directly necessary if they themselves are displayed. Some events are indirectly needed because a "displayed" event may be defined in terms of a non-displayed event.

In a preferred embodiment, event generator 24 is triggered every 60 seconds. Upon being triggered, event generator 24 checks the database to see if any new events were selected for display, or whether any events were modified. If so, the event generator 24 analyzes patient information corresponding to the newly added or newly modified event defintion for the entire duration selected by the user. For any events that are unchanged, the event generator analyzes patient information corresponding to the intervening period from the last analysis.

The present invention can operate for many patients. As such, the stored patient information is organized according to patient identifications. The event generator 24 includes management routines to handle initialization of any new data structures for newly added patients, as well as for deleting the appropriate data structures when they are no longer needed, for example when a patient is released.

Optionally, event generator 24 can read and/or write access a second database 25 that, in turn, accesses a second disk system 26. Second database 25 would store non-bedside information, such as lab results, a patient's prior medical history, and the like. Second database 25 and second disk system 26 would likely be located on the LAN 13 (see FIG. 2).

Figure 4:
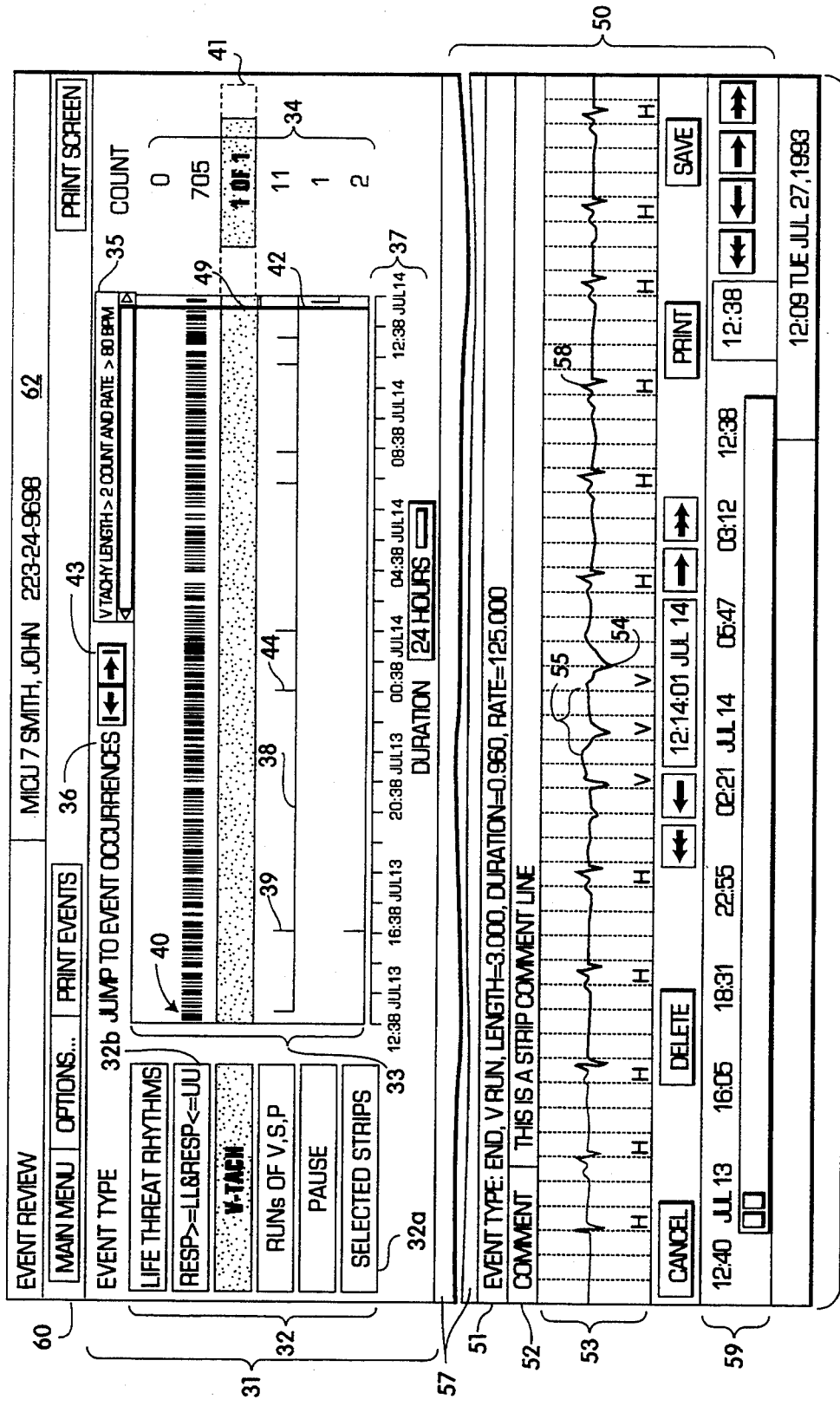
FIG. 4 is a main screen display generated in accordance with a preferred embodiment of the present invention.

FIG. 4 illustrates a main screen display 30 generated by the ERA 28 of a preferred embodiment. The main screen display 30 provides an ergonomic layout that concisely presents a substantial amount of patient information, while remaining uncluttered. In addition, this layout provides user functionality to efficiently navigate through the data sequentially or randomly. It will be appreciated that the invention is in no way limited to this particular layout.

The patient's name and other information, such as ID number, are displayed in section 62. A menu bar 60 includes several menu buttons for main menu, options, print events, and print screen. Activating the main menu button displays a list of application entries, such as quit and help. The print screen menu button, when activated, prints a screen dump of the display. The print events menu button prints the event time lines. The options menu button, when activated, activates ancillary menus, such as an Event Review Options Dialog box, described below.

An event search and selection area 31 includes a selected event type region 32, an event occurrence region 33, an event count region 34, a selected event definition region 35, a sequential search control region 36, and an event time scale region 37.

The selected event type region 32 shows the event names for the event type definitions that are selected for display. Each event name is shown on a toggle button 32a, which, when activated, selects an event time line 38. The reason for selecting a time line is discussed below.

Event occurrence region 33 displays several horizontal event time lines 38. Tick marks 39 indicate the occurrence of the corresponding event. In other words, tick marks indicate each instance when all the conditions for the corresponding event type definition have been satisfied, as detected by event generator 24. When events occur at a high rate relative to the duration of the time line, solid blocks 40 appear. Moreover, if two or more occurrences are relatively close in time, only one tick mark will appear. In any case, the event count, described below, accurately reflects the actual number of event occurrences. The process for managing this is discussed below.

The event occurrence region 33 is extremely helpful to the clinician because clinicians prefer to think in terms of events and not necessarily in terms of physical measurements or trend data. Thinking in terms of physical measurements can be complicated and time consuming, especially in instances when the clinician is interested in a logical, mathematical, or time relation among different measured quantities. In such instances, prior art systems required the user to view separate waveforms or trend data and perform the relations mentally. The clinician who uses the present invention, however, can simultaneously view numerous events without expending such mental effort. In addition, unlike the prior art, the clinician can interactively and iteratively create or modify definitions to aid in his or her analysis. Furthermore, he or she can scan through events either randomly or sequentially.

The event count region 34 displays the number of occurrences of the corresponding events during the duration of the event time line 38. As shown, the time line for event V-TACH 41 is selected, which has its only occurrence selected (the process of selecting an occurrence is described below). Accordingly, event count region 34 indicates that event "1 of 1" is selected. This means that there was one occurrence of the event within the selected duration (described below) and the first occurrence is selected. For all of the other events, the total number of occurrences for the corresponding time line is indicated in event count region 34.

The selected event definition region 35 indicates the definition for the selected event time line. This is helpful because the selected event, V-TACH, can be defined differently for different patients, i.e., V-TACH for patient 1 may correspond to a first threshold, while for patient 2 it may be defined with a second threshold. The selected event definition region 35 allows the clinician to check the particular definition for the patient.

Moving the system cursor, not shown, into the event time scale region 37 results in the cursor changing its icon shape, not shown, indicating to the user that he can change the time duration of event occurrence region 33 directly from the display 30. The time origin is also manipulable. For example, if the duration is one hour, the user can select any hour for which the database 22 has data, and he or she is not limited to merely the last hour. As will be further described below, the duration of the event time scale region 37 can be changed in other manners, such as via an Event Review Options Dialog Box.

Users can navigate through the patient's event history by either randomly or sequentially selecting event occurrences. A particular occurrence of an event 49 can be randomly selected by moving the system cursor, not shown, near the desired occurrence's tick mark. Upon activating the cursor, the nearest tick mark within the selected time line 41 is selected. Upon such selection, an event cursor 42 will align with the selected occurrence. Random selection can also be performed by moving and activating the cursor very near the desired tick mark, even if the corresponding time line is not selected. In this case, the desired event occurrence and the corresponding time line are both selected. If a new event time line is selected by activating an event type toggle button 32a, the event occurrence of the newly selected event time line that is nearest in time to the previously selected event occurrence is automatically selected.

Event occurrences can also be selected sequentially via the sequential search controls 43 of the sequential search control region 36. Sequential selection is performed with respect to a selected event time line. For example, if the event occurrence corresponding to the tick mark 39 was already selected, event time line 38 being already selected, activating search control toggle button 43 advances the event cursor 42 to event occurrence 44, the next event occurrence.

Upon selecting a particular event occurrence 49, additional information particular to that event type and/or that event occurrence can be displayed in a specific event display region 50. For example, waveform area 53 displays the particular waveform strip 58 for event 49. This waveform strip 58 may supply additional useful information to the clinician. For example, assume event V-TACH is defined as a measurement reaching a certain amplitude. Though the tick mark 49 indicates that the amplitude has been reached, waveform strip 58 displays a complete representation of the corresponding measurement. The surrounding waveform region 55 may supply other hints to aid the clinician's analysis. The time duration for the waveform strip is typically much smaller than the duration for the event time lines, e.g., 8 seconds for the waveform strip versus 24 hour duration for the event time line.

Event type region 51 includes additional information about the event, such as whether the event is displayed for the beginning or the end of the event. Several other parameters are included, such as duration, rate, and length.

An additional information region 57 is used to display text, images, or other information for the selected event or the selected event occurrence. For example, region 57 may be used to display radiology or other images corresponding to the event or the occurrence. It will be appreciated that this additional information may be sourced from databases other than that of the patient's information, for example, if the displayed data concerned lab results.

Time selection controls in a time selection control region 59 allow the user to manipulate the time duration for the system. Typically data is stored for a twenty-four hour period. However, the mechanisms and invention described herein are easily adaptable to longer or shorter durations, the limiting factor being the cost of the hardware. Though the description refers to selection of a particular time duration via the several time controls, the invention is easily adaptable to automatic scrolling of event time lines to keep the main screen 30 current. In other words, the event generator 24 and ERA 28 may be triggered periodically to update the screen, rather than triggering by action of the user, such as selecting a new time duration or new definition for display.

Figure 5:
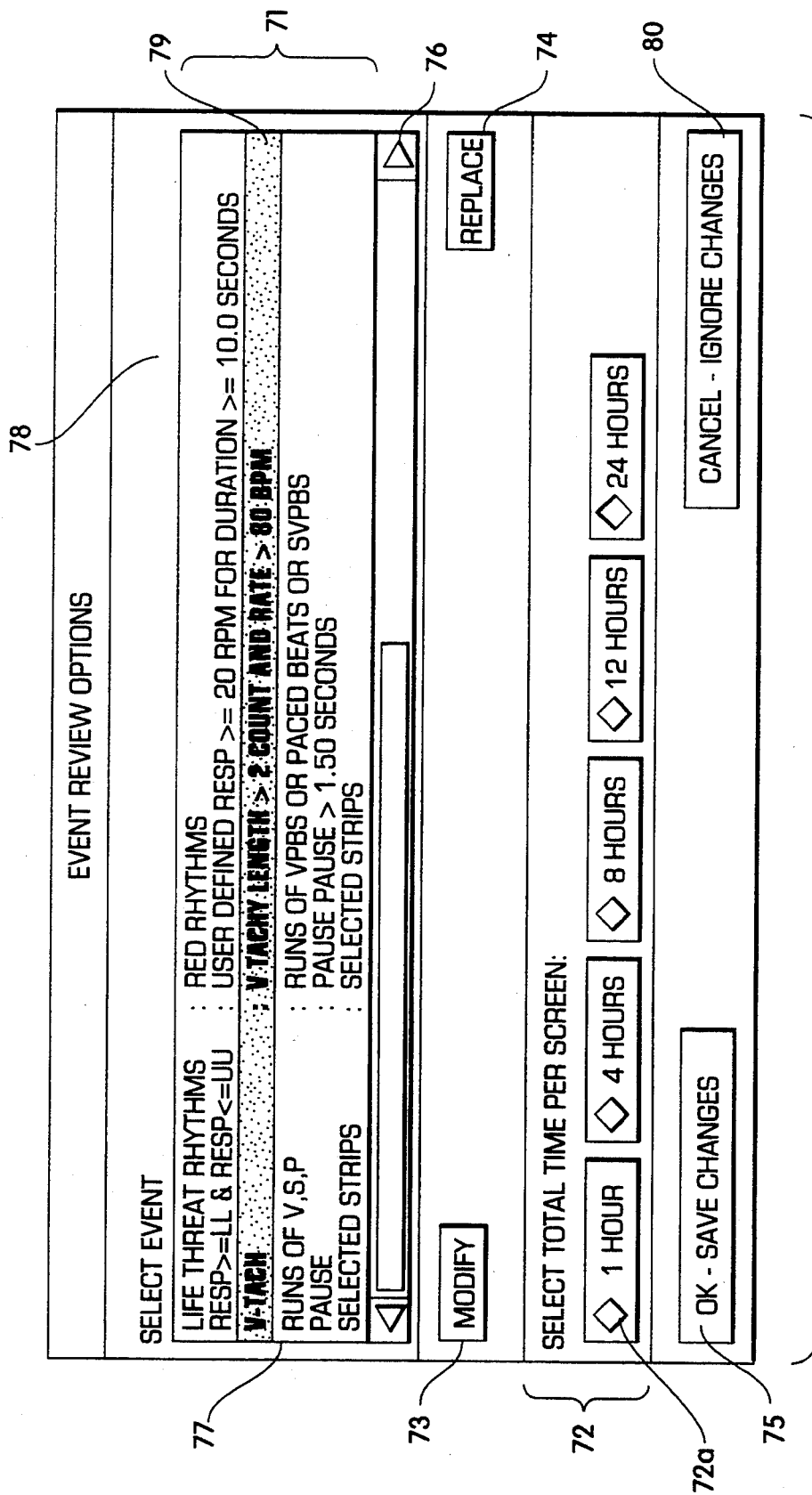
FIG. 5 is a screen display for an Events Review Options Display Box generated in accordance with a preferred embodiment of the invention.

FIG. 5 illustrates the Event Review Options Dialog box 70, which is activated via the options menu button described above. This dialog box provides the user with an additional way to modify the duration of the event time lines via a select total time per screen region 72 having a series of toggle buttons 72a.

The Event Review Options Dialog box 70 also allows the user to modify or replace the event types that are selected for display. A select event region 71 includes an event name region 77 and an event definition region 78. The event name region 77 lists the names of the events that are selected for display on event type name region 32 of the main screen 30. The event definition region 78 displays the corresponding event definitions. Scroll bar 76 allows the user to display the unseen portions of the definition.

A particular event name and event definition 79 can be selected via the system cursor. A modify toggle button 73 allows the clinician to modify the particular name or the particular definition. Upon activating the modify toggle button 73 a Modify Event Dialog box 100, as shown in FIG. 7 is activated.

Figure 7:
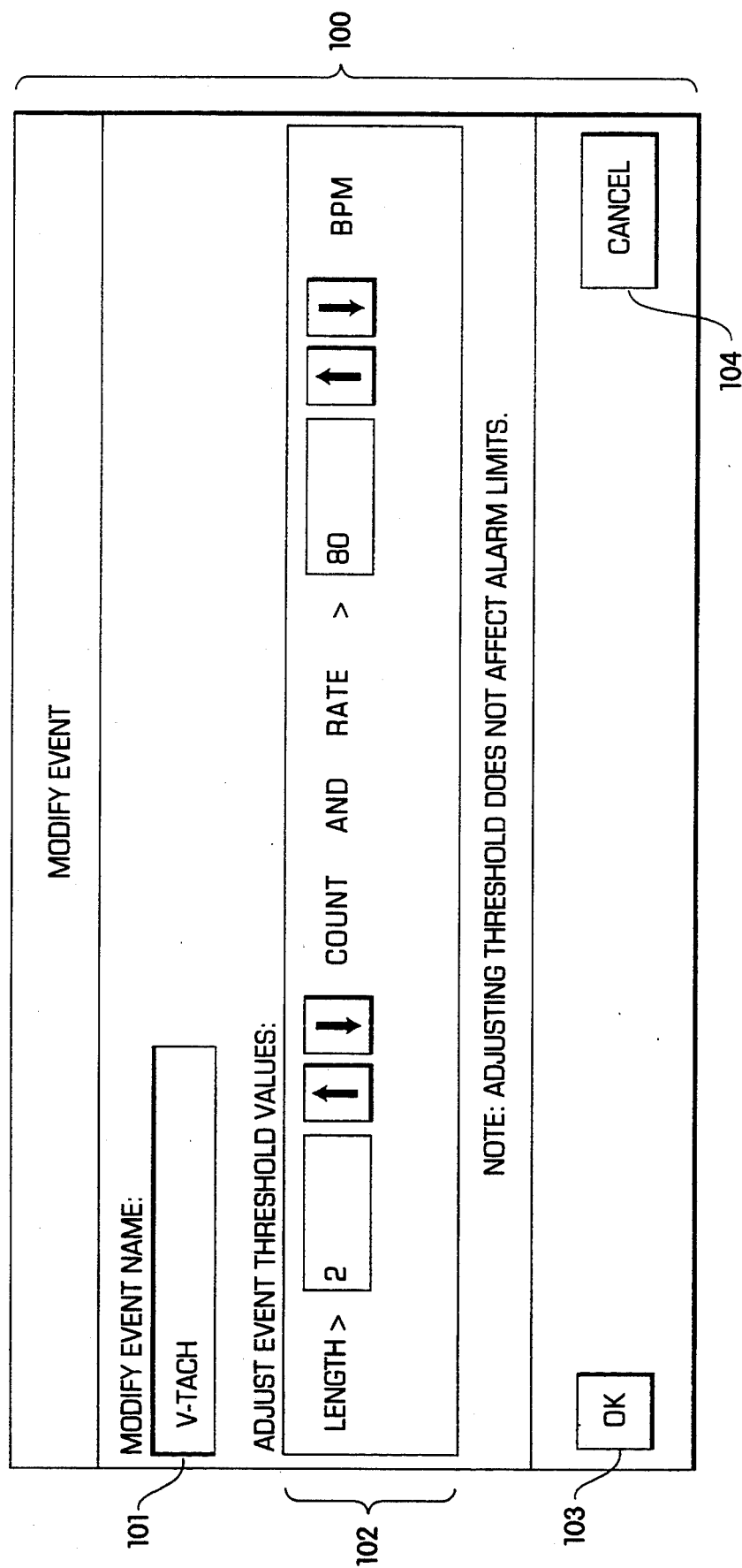
FIG. 7 is a screen display for a Modify Event Dialog Box generated in accordance with a preferred embodiment of the invention.

The Modify Event Dialog box 100 shown in FIG. 7 allows the user to modify the event name via a modify event name region 101 or to adjust the particular thresholds via a threshold region 102. Toggle button 103 allows the modification to be saved and toggle button 104 allows the user to cancel the modify operation. A save changes toggle button 75 (FIG. 5) stores the changes in the database.

Figure 6:
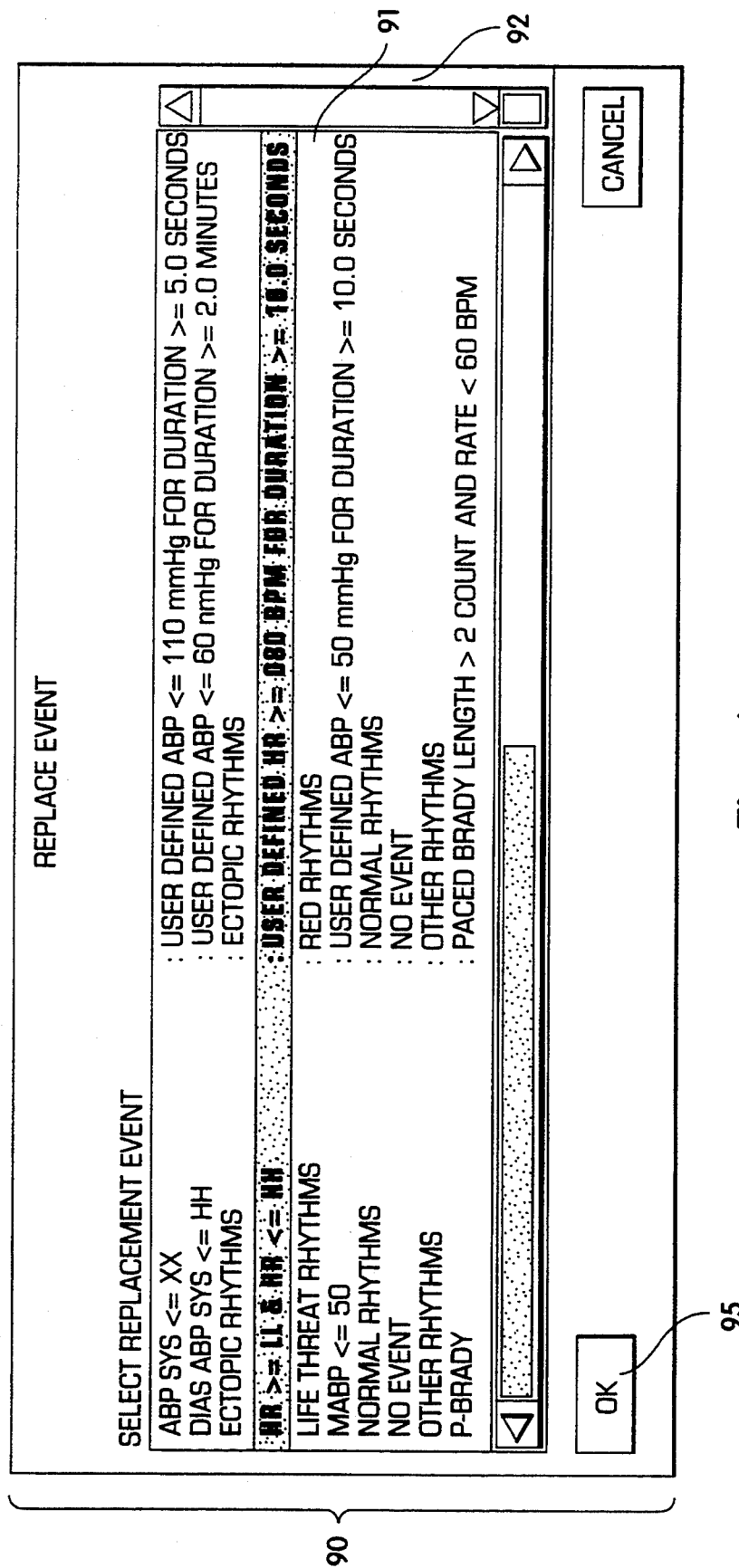
FIG. 6 is a screen display for a Replace Event Dialog Box generated in accordance with a preferred embodiment of the invention.

As previously described, the database contains an event type dictionary. If the clinician prefers to replace one of the events selected for display with an event definition from the dictionary, he or she must select the event name to be replaced. Upon activating a replace toggle button 74, a Replace Event Dialog box 90, as shown in FIG. 6 is activated. The Replace Event Dialog box 90 provides a list of the entire event name dictionary contents via a dictionary region 91 and a scroll bar 92. Activating an OK toggle button 95 completes the replacement process.

In a preferred embodiment, the ERA 28, including the layout and functionality described above, is implemented using Motif. Motif is a graphics package known in the art that allows user-applications to be linked with the graphics functionality provided by the package. A basic operational unit of Motif is a "widget," which is akin to a data structure. Widgets may be Motif defined or application defined. The widget definition, in turn, dictates which user operations the widget is sensitive to. For example, Motif provides a "toggle button" widget, which will trigger a corresponding routine if the user single clicks the mouse in the pixel space of that toggle button widget. The underlying application defines the screen in terms of widgets and provides the corresponding routines for those widgets. Motif provides the screen management functionality to keep track of the various widgets' pixel space and to determine if a user activity, e.g., single or double click mouse, has occurred in a widget's pixel space. In a preferred embodiment, the main screen (30, FIG. 4) is comprised of widgets and the functionality described in conjunction with the main screen is provided by the corresponding routines. For example, in a preferred embodiment, the event name toggle buttons 32a are toggle button widgets, which, when activated by a click, call routines to select the corresponding event time line 38. As both Motif and widgets are known in the art further description of Motif and widgets is not provided for the sake of clarity.

The event occurrence region 33 utilizes ERA defined widgets called "line plot widgets." Line plot widgets display a graph, when given a set of coordinates. In contrast, the toggle button widgets, described above, display text, which usually label the corresponding toggle button, e.g., "V-TACH." This graph includes a set of tick marks if an array of coordinates for the tick marks is provided. As such, each event time line 38 with corresponding tick marks is a line plot widget. These widgets are sensitive to mouse clicks and have routines that will select a particular event occurrence if that widget is clicked, as described above. This selection will include triggering a display of a waveform strip corresponding to that event occurrence and a display of other data as described above.

The plotting and selecting of tick marks within a line plot widget utilizes an overplotting algorithm to hash, or map, tick mark data, i.e., the time instance of the event occurrence, into coordinate, or pixel, data for the tick mark. This overplotting algorithm considers the size of the event occurrence region and the length of time corresponding to that region. A single pixel may hash to a time quantum that contains more than one event occurrence. As such, even if a mouse could accurately point to a single pixel, it would still be impossible to randomly select a particular occurrence if more than one occurrence corresponded to that pixel. The overplotting algorithm, however, manages this by hashing the pixels to the correct event occurrences. As such, sequential and random selection of event occurrences operates correctly. The overplotting algorithm hashes event occurrence data into pixel data and vice-versa. As hashing techniques are known in the art, a fuller description of hashing functionality is not provided for the sake of clarity.

In a preferred embodiment, each event type of the selected event type region 32 is processed as a group. For example, if a user changes the duration of the event time scale regions 37, each event 32a, and in particular each event time line 38, will be updated. That is, the event generator 24 will be triggered to monitor the patient information for the newly selected time period and in accordance with all the directly and indirectly necessary event type definitions. The database 22 will inform ERA 28 upon completion, and the ERA 28 will display all the corresponding event time lines and tick marks. In similar fashion, if an event definition is modified, or if an event is replaced, the entire set of directly and indirectly necessary events will be monitored and displayed.

The ERA 28 itself is triggered from either ERA specific requests, such as clicking an event name toggle button 32a, or from actions that cause the ERA to need new data, such as replacing an event for display, modifying an event, or changing the time period for display. These latter actions cause the ERA 28 to suspend itself until the database 22 informs the ERA 28 that the Event Generator 24 has completed its data monitoring. An initialization sequence will also trigger the ERA 28 to create a main screen with a default set of widgets, which correspond to a default set of event types.

It will be appreciated by those skilled in the art that the ERA 28 is one software process. Motif provides the screen management, and as such, calls the routines corresponding to the numerous widgets.

EDL 27 provides a database search language, further described below, for the user to create and modify event type definitions. These definitions may be created or modified on a per patient basis so that the clinician can tailor the definitions to aid his analysis. The language provides an ergonomically advantageous syntax so that clinicians, not just computer scientists, can easily create definitions. Moreover, to supplement the ergonomically advantageous language, EDL 27 provides a graphical interface to facilitate the entry of definitions in the database.

Figure 8:
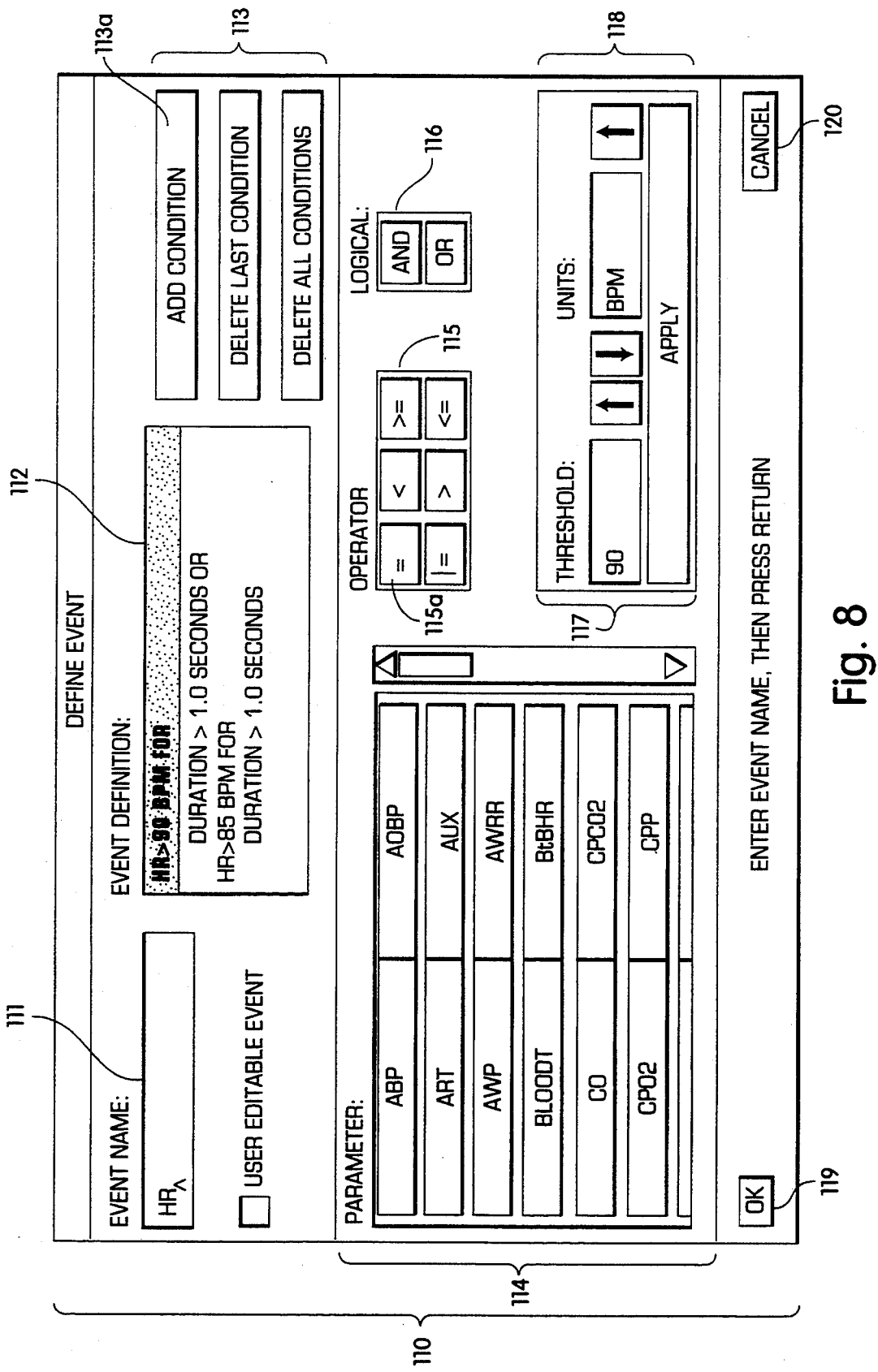
FIG. 8 is a screen display for an Event Definition Dialog Box generated in accordance with one embodiment of the invention.

As previously described, EDL 27 allows the user to interactively define new event types. FIG. 8 illustrates an Event Definition Dialog box 110 that is displayed upon activating one embodiment of EDL 27. EDL 27 can be activated from the system screen, not shown, or from the main screen 30 via the main menu button.

The Event Definition Dialog box 110 includes an event name region 111, an event definition region 112, control region 113, a parameter region 114, an operator region 115, a logical region 116, a threshold region 117, units region 118, OK toggle button 119, and a cancel toggle button 120. The event name region 111, when selected, allows the user to enter an event name for the event to be created. The event definition region 112 shows the definition for that event. The control region 113 includes a series of toggle buttons 113a that allow the user to add or delete some or all of the conditions for the particular definition. The parameter region 114 includes a list of all condition parameters that can be used in an event definition. Optionally, this list can include events as well as physical measurements. Operator region 115 includes a series of toggle buttons 115a to use in creating the relationships that define the new event. Likewise, logical region 116 includes a series of toggle buttons 116a that are used for logical relationships. Threshold region 117 and units region 118 with their associated control toggle buttons are used to further define a particular event. OK toggle button 119 instructs the EDL 27 to add the new event to the event type dictionary in the database. Activating the OK toggle button will subject the new event type definition to a syntax check, further described below. Cancel toggle button 120 cancels the operation.

Figure 9:
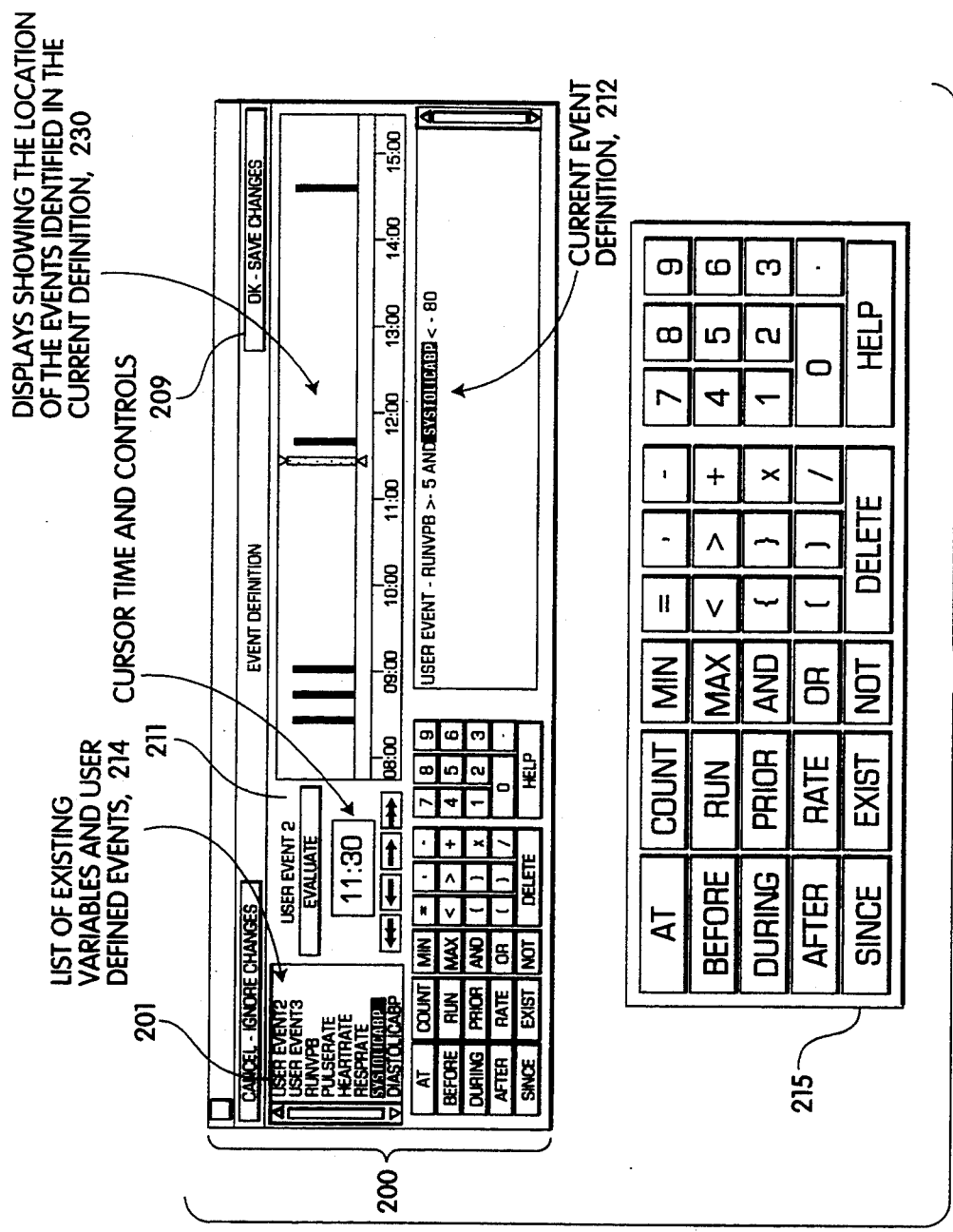
FIG. 9 is a screen display for an Event Definition Dialog Box generated in accordance with a preferred embodiment of the invention.

FIG. 9 illustrates an Event Definition Dialog box 200 for a preferred embodiment of the invention. This dialog box includes a powerful set of operators for a preferred embodiment of the event definition language. This preferred language includes simple numeric events, compound events, numeric operations, non-numeric events, event timing, and other language constructs. As indicated at 201, this embodiment allows events to be defined in terms of other events.

The event definition dialog box 200 includes an event name region 211 and an event definition region 210, a parameter region 214, an operator region 215, and a OK toggle button 209. The event name region 211 and the parameter region 214 are similar to the corresponding regions described above in connection with FIG. 8. Operator region 215, however, is substantially different in that it provides a more complete and more powerful set of operators. Among other features, this powerful set of operators includes numeric operations, such as COUNT and RUN, which are described below. In addition, this set of operators includes timing relationships, such as AFTER, BEFORE, and DURING. Lastly, other language constructs such as MINIMUM, PRIOR, RATE, and EXIST are included. Event occurrence display region 230 displays the event occurrence identified for the current definition. In this manner, it provides the user a better tool to interactively and iteratively develop an event definition. For example, when the user enters a new definition he or she will instantly see whether the new definition is useful, i.e., whether it provides too much or too little information.

The various dialog boxes for EDL 27 described above are likewise implemented using Motif, in a preferred embodiment. The various functions described above are implemented as software routines corresponding to the various widgets and user activity.

A pseudo-Backus-Nauer representation of the preferred language is included in Appendix A. However, the following informal description will also be helpful in understanding the language. It is important to note that, among other things, the preferred embodiment includes compound events, which are a combination of relationships, besides including the more powerful set of operators that were just described.

1 Simple Numeric Events

The simplest event is a relationship between a variable and a value such as:

$$HR \leq 60$$

This basic relationship can be generalized to
"event: numericVar numericRelationOp numericConst"
where "numericRelationOp" is any of the standard equality or inequality operators:

$$= \geq \leq > < !=$$

The simple heart rate event shown above is equivalent to $$60 \geq HR$$

Therefore, an even more general way to express a basic event is
"event: numeric numbericRelationOp numeric
where "numeric" is a "numericConst" or a "numericVar."

Note that the following event specification is also valid:

$$HR != PULSE$$

2 Compound Events

An event can be a combination of relationships such as $$HR > 150 \text{ AND } systolicABP \leq 80$$

This event has occurred only if the heart rate measurement is greater than 150 and the systolic arterial blood pressure is less than or equal to 80. Similarly, events can be combined with the OR operator, as in:

$$HR \leq 60 \text{ OR } PULSE \leq 60$$

These two events can be generalized as
"event: event binaryLogicalOp event
where "binaryLogicalOp" is either AND or OR.

The availability of two logical operators necessitates a precedence rule. EDL adopts the usual convention of evaluating AND before OR. Parentheses can be used to override this precedence convention. For example, the following is a valid event specification:

$$(HR \leq 60 \text{ AND } HR > 0) \text{ OR } (PULSE \leq 60 \text{ AND } PULSE > 0)$$

The NOT operator is also included. For example, the event specification:

$$NOT\ HR > 60$$

is equivalent to the event specification:

$$HR \leq 60$$

3 Numeric Operations

The four arithmetic operators can be used to combine numerics. Therefore, the following is a valid numeric:

$$(systolicABP - diastolicAB) \times HR$$

EDL adopts the usual convention of evaluating $\times$ and $\div$ prior to $+$ and $-$. Once again, parentheses can be used to override this convention.

A numeric can also be generated by counting the number of occurrences of an event. The following numeric equals the total number of occurrences of tachycardia in the entire patient record:

$$COUNT\ HR > 120$$

The following numeric equals the number of consecutive high heart rates:

RUN HR>120

4 Nonnumeric Events

Not all patient data is numeric. Therefore, EDL supports both ordinal (nonnumeric values that can be ordered) and categorical values (nonnumeric values that cannot be ordered). For example, the following event occurs if there are 10 consecutive beats that are labeled "V":

(RUN beatLabel=V)≧10

Similarly, the following event occurs if a urine glucose measurement (an ordinal variable) is greater than "++":

urineGlucose>++

5 Event Timing

Some events are significant only if they occur in the context of another event. For example, the following event occurs if bradycardia follows a ventricular beat:

HR≦60 AFTER beatLabel=V

The following is an equivalent expression of this event beatLabel=V BEFORE HR≦60

Similarly, the following event occurs if there is bradycardia during a run of ventricular beats:

HR≦60 DURING beatLabel=V

In general, these events are of the form:
"event: event timingRelationship event"
where "timingRelationship" is BEFORE, AFTER or DURING.

The example using AFTER would not be useful clinically because the specified event occurs if bradycardia occurs at any time following a ventricular beat. The SINCE function can be used to express a more specific event definition:

(HR≦60 AFTER beatLabel=V) AND (SINCE beatLabel=V<MINUTE

The following statement is a numeric that equals the heart rate when the last ventricular beat occurred:

AT (beatLabel=V) HR

The general form of this expression is:
"numeric": AT "event numeric"
Similar expressions are valid for ordinary and categorical values.

A time point (e.g., Sep. 29, 1990 10:00 PM) is treated as an event. Therefore, the following event occurs only if bradycardia occurs after 10:00 PM on Sep. 29, 1990:

HR≦60 AFTER Sep. 29, 1990 10:00 PM

6 Other Language Constructs

EDL includes several language constructs that simplify the definition of events. One of these is the notion of a set of values. For example, the following event excludes beats that are labeled "L" or "?":

beatLabel!={L,?}

This statement is shorthand for (beatLabel!=L) AND (beatLabel!=?)
The general form is
"event:value relationOp {value, . . . ,value?}"
The event occurs if the relationship is true for all of the terms in the set.

EDL provides MINIMUM AND MAXIMUM operations that determines the extreme values for numeric or ordinal values. For example, the following expression equals the minimum heart rate:

MINIMUM HR

The extreme operators can be combined with the AT operator, as in

AT (beatLabel=V) MINIMUM HR which determines the minimum heart rate during ventricular beats.

The following statement returns the patient's previous heart rate:

PRIOR HR

The general form of this statement is PRIOR "variable"
where "variable" is a numeric, ordinal or categorical valued variable.

The following statement returns the rate of change in the patient's heart rate, in units per minute:

RATE HR

The value returned by this statement is computed by subtracting the previous heart rate from the current heart rate and dividing the result by the length of the time interval between these two measurements. The general form for this statement is RATE "numericVar"

Finally, the following event occurs whenever cardiac output is measured:

EXIST cardiacOutput

The EXIST operator can be combined with a list of variables to specify an event that occurs if values are available for all of the listed variables.

The preferred language may be implemented with the standard UNIX utilities lex() and yacc(). These utilities are used to perform the parsing of the event definitions. The lex() utility is used to identify the tokens of the language, and the yacc() utility is used to specify the grammar for combining these tokens. Assuming that the entered event definition passes the syntactical checks corresponding to this preferred language, the EDL 27 then creates a data structure describing the new event and passes this new data structure to the database 22. As previously described, this new event will be added to the event type dictionary, where it will be available for the user to select for display or for the user to indirectly access as another variable for yet another new event type definition. Those skilled in the art will understand the combination of lex(), yacc(), and the Appendix A definition for implementing the EDL languages.

While there have been shown and described what are at present to be considered the preferred embodiments of the present invention, it will be obvious to those skill in the art that there is changes and modifications may be made without departing from the scope of the invention as defined by the appended claims.

APPENDIX A

The statement

X:Y indicates that construct X is defined by construct Y. A list of two or more constructs, without separators, indicate that the first construct in the list is followed by the second construct in the list and so forth. Therefore, the following statement indicates that X is defined to be Y followed by Z:

X: Y Z

A list of two or more constructs, separated by vertical bars ("|"), indicates the alternative representations for a construct. Therefore, the following statement indicates that construct X is defined to be either Y or Z:

X:Y|Z

The following tokens are treated as literals:

| AFTER | DURING | NOT | SINCE |
|-------|--------|-----|-------|
| AND | EXIST | OR | = != |
| AT | HOURS | PRIOR | ( ) |
| BEFORE | MAXIMUM | RATE | { } |
| BEFORE | MINIMUM | RUN | + - ÷ x |
| DAYS | MINUTES | SECONDS | > < ≥ ≤ |

For example, if X, Y and Z denote relationships then

X:Y OR Z indicates that relationship X is the union of relationships Y and Z. Similarly, the following statement indicates that construct X is defined to be constructs Y and Z separated by a comma:

X:Y,Z

The following tokens represent the corresponding constants and variables:

NUMERIC_CONSTANT    NUMERIC_VARIABLE
    ORDINAL_CONSTANT    ORDINARL_VARIABLE
    CATEGORICAL_CONSTANT    CATEGORICAL_VARIABLE

The token NAMED-EVENT represents a previously defined event. The token TIME-POINT represents a point in time, such as 10:00PM on 29Sep90.

Finally, the following is a list of the various operators in order of increasing precedence:

1. { }
2. ,
3. COUNT RUN PRIOR RATE
4. AT
5. AFTER BEFORE DURING
6. OR
7. AND
8. NOT
9. DELTA
10. MAXIMUM MINIMUM
11. = $\geq$ > $\leq$ < !=
12. + −
13. x ÷
14. ( )

The highest level construct in EDL search language is an event:

```
event              : (event)
                   | expression
                   | event AND event
                   | event OR event
                   | NOT event
                   | event timeRelation event
                   | event timeRelation {eventList}
                   | EXIST variable
                   | EXIST {variableList}
                   | NAMED-EVENT
                   | SINCE event relation numeric timeUnit
                   | TIME-POINT timeRelation       : AFTER
                   | BEFORE
                   | DURING relation           : =
                   | $\geq$
                   | >
                   | $\leq$
                   | <
                   | != eventList          : event
                   | eventList , event variable           : (variable)
                   | NUMERIC_VARIABLE
                   | ORDINAL_VARIABLE
                   | CATEGORICAL_VARIABLE variableList       : variable
```

```
                        | variableList , variable expression          : numericExpression
                        | ordinalExpression
                        | categoricalExpression numericExpression   : numeric relation numeric
                        | numeric relation {numericList} numeric             : ( numeric )
                        | NUMERIC_CONSTANT
                        | NUMERIC_VARIABLE
                        | numeric + numeric
                        | numeric - numeric
                        | numeric X numeric
                        | numeric ÷ numeric
                        | COUNT event
                        | RUN event numeric
                        | AT event numeric
                        | MAXIMUM numeric
                        | MINIMUM numeric
                        | PRIOR NUMERIC_VARIABLE
                        | RATE NUMERIC_VARIABLE numericList         : numeric
                        | numericList , numeric ordinalExpression   : ordinal relation ordinal
                        | ordinal relation { ordinalList } ordinal             : ( ordinal )
                        | ORDINAL_CONSTANT
                        | ORDINAL_VARIABLE
                        | AT event ordinal
                        | MAXIMUM ordinal
                        | MINIMUM ordinal
                        | PRIOR ORDINAL_VARIABLE ordinalList         : ordinal
                        | ordinalList , ordinal categoricalExpression   : categorical = categorical
                            | categorical = {categoricalList}
                            | categorical !=categorical
                            | categorical !={categoricalList} categorical         : (categorical )
                        | CATEGORICAL_CONSTANT
                        | CATEGORICAL_VARIABLE
                        | AT event categorical
                        | PRIOR CATEGORICAL_VARIABLE
```

```
categoricalList        :   categorical
                       |   categoricalList , categorical
```

What is claimed is:

1. In a medical information system comprising a patient monitoring device for acquiring physiological parameters from a patient, a computer system for processing the physiological parameters acquired from the patient to provide medical information and a display unit for displaying said medical information to a user, a method for identifying and displaying events wherein said medical information system executes steps comprising:

establishing an event associated with the patient, said event being defined by a user in an event definition language, said event including an event definition which defines the event as having an occurrence when one or more of said physiological parameters meets a prescribed condition;

acquiring said physiological parameters in real time;

monitoring the acquired physiological parameters for occurrences of said event; and informing the user of the occurrences of said event.

2. A method as defined in claim 1 wherein the step of informing the user includes displaying the occurrences of said event as a function of time on said display unit.

3. A method as defined in claim 1 wherein the step of informing the user includes displaying the occurrences of said event on a timeline on said display unit.

4. A method as defined in claim 3 wherein the step of informing the user further includes displaying a count of occurrences of said event on said display unit.

5. A method as defined in claim 3 wherein the step of informing the user further includes displaying detailed information on said display unit regarding an occurrence of said event selected by the user.

6. A method as defined in claim 5 wherein the step of displaying detailed information includes displaying a waveform of one of said physiological parameters in a time interval corresponding to the occurrence of said event selected by the user.

7. A method as defined in claim 1 wherein the step of monitoring the acquired physiological parameters includes monitoring the acquired physiological parameters as they are acquired from the patient.

8. A method as defined in claim 1 further including storing the physiological parameters which are acquired over a prescribed time period and wherein the step of monitoring the acquired physiological parameters includes searching the stored physiological parameters for occurrences of said event.

9. A method as defined in claim 1 further including storing the physiological parameters acquired over a prescribed time period and establishing a new event after acquisition and storage of said physiological parameters and wherein the step of monitoring the acquired physiological parameters includes searching the stored physiological parameters for occurrences of said new event.

10. A method as defined in claim 1 further including storing said event occurrences for subsequent display on said display unit in response to user selections.

11. A method as defined in claim 1 wherein the step of establishing an event includes defining said event by a relationship in said event definition language between one of said physiological parameters and a numeric value.

12. A method as defined in claim 1 wherein the step of establishing an event includes defining said event by a relationship in said event definition language involving a logical combination of two or more conditions met by said physiological parameters.

13. A method as defined in claim 1 wherein the step of establishing an event includes defining said event by a relationship in said event definition language involving an arithmetic operation upon one or more of said physiological parameters.

14. A method as defined in claim 1 wherein the step of establishing an event includes defining said event by a relationship in said event definition language involving a timing operation with respect to one or more of said physiological parameters.

15. A method as defined in claim 1 wherein the step of establishing an event includes defining said event by a relationship in said event definition language involving a minimum or maximum value of one of said physiological parameters.

16. A method as defined in claim 1 wherein the step of establishing an event includes defining said event by a relationship in said event definition language involving one or more previously defined events.

17. A medical information system comprising:

a patient monitoring device for acquiring physiological parameters from a patient;

a computer system for processing the physiological parameters acquired from the patient to provide medical information;

a display unit for displaying said medical information to a user;

said computer system including;

means for establishing an event associated with the patient, said event being defined by the user in an event definition language, said event including an event definition which defines the event as having occurrence when one or more of physiological parameters meets a prescribed condition, means for monitoring the acquired physiological parameters for occurrences of said event, and means for displaying the occurrences of said event on said display unit.

* * * * *